United States Patent [19]

Cummins

[11] Patent Number: 5,333,608
[45] Date of Patent: Aug. 2, 1994

[54] ENDOTRACHEAL TUBE FOR FACE, CHIN AND NECK SURGERY

[75] Inventor: Christopher K. M. Cummins, Tullamore, Ireland

[73] Assignee: Sherwood Medical Company, St. Louis, Mo.

[21] Appl. No.: 954,182

[22] Filed: Sep. 30, 1992

[51] Int. Cl.$^5$ .................................................. A61M 16/00
[52] U.S. Cl. ................................ 128/207.14; 128/912; 128/207.15
[58] Field of Search ............... 285/423, 272, 280, 278; 128/911, 912, 207.14, 207.17, 207.18, DIG. 26, 207.15, 204.18, 202.27; 604/283, 905, 408, 243

[56] References Cited

U.S. PATENT DOCUMENTS

| | | | |
|---|---|---|---|
| 1,911,423 | 5/1933 | Biller | 285/278 |
| 2,764,430 | 9/1956 | Roberts | 285/278 X |
| 2,912,982 | 11/1959 | Barsky | 128/207.14 |
| 3,388,705 | 6/1968 | Grosshandler | 128/207.14 |
| 3,599,642 | 8/1971 | Tindel | 128/207.14 |
| 3,670,726 | 6/1972 | Mahon et al. | 128/204.18 |
| 3,747,812 | 7/1973 | Karman | 222/387 |
| 3,814,103 | 6/1974 | Fettel et al. | 128/207.18 |
| 3,824,999 | 7/1974 | King | 128/207.14 |
| 3,848,605 | 11/1974 | Harautuneian et al. | 128/207.15 |
| 3,858,615 | 1/1975 | Weigl | 138/121 |
| 3,948,274 | 4/1976 | Zeldman et al. | 128/207.14 |
| 3,964,488 | 6/1976 | Ring et al. | 128/207.14 |
| 3,972,321 | 8/1976 | Proctor | 128/207.17 |
| 4,022,219 | 5/1977 | Basta | 128/207.14 |
| 4,033,353 | 7/1977 | La Rosa | 128/207.15 |
| 4,050,466 | 9/1977 | Koerbacher | 128/207.14 |
| 4,152,017 | 5/1979 | Abramson | 285/260 |
| 4,166,467 | 9/1979 | Abramson | 128/207.14 |
| 4,240,417 | 12/1980 | Holever | 128/203.12 |
| 4,296,949 | 10/1981 | Muetterties | 285/18 |
| 4,351,328 | 9/1982 | Bodai | 128/202.16 |
| 4,377,164 | 3/1983 | Sabbota | 128/207.14 |
| 4,378,012 | 3/1983 | Brown | 128/207.17 |
| 4,416,273 | 11/1983 | Grimes | 128/207.16 |
| 4,471,776 | 9/1984 | Cox | 128/207.15 |
| 4,588,402 | 5/1986 | Igari | 604/408 |
| 4,593,690 | 1/1986 | Sheridan et al. | 128/207.15 |
| 4,612,929 | 9/1986 | Schubert et al. | 128/204.25 |
| 4,622,965 | 11/1986 | Teeple | 128/207.14 |
| 4,676,241 | 6/1987 | Webb et al. | 128/207.14 |
| 4,852,564 | 8/1989 | Sheridan et al. | 128/202.27 |
| 5,024,220 | 6/1991 | Holmgreen et al. | 128/207.18 |
| 5,054,482 | 10/1991 | Bales | 128/207.14 |
| 5,062,420 | 11/1991 | Levine | 128/204.18 |
| 5,065,756 | 11/1991 | Rapoport | 128/204.18 |
| 5,078,131 | 1/1992 | Foley | 128/203.15 |
| 5,184,611 | 2/1993 | Turnbull | 128/207.14 |
| 5,245,992 | 9/1993 | Nye | 128/200.26 |

FOREIGN PATENT DOCUMENTS

| | | | |
|---|---|---|---|
| 146688 | 2/1981 | German Democratic Rep. | 128/207.18 |
| 274138 | 7/1927 | United Kingdom | 285/280 |

*Primary Examiner*—Edgar S. Burr
*Assistant Examiner*—Eric P. Raciti
*Attorney, Agent, or Firm*—Andrew J. Beck; Montgomery W. Smith; Curtis D. Kinghorn

[57] ABSTRACT

A tracheal tube having a distal end for placement in a patient's trachea. In one embodiment, the tracheal tube includes a preformed curved proximal end that directs the tracheal tube, upon leaving the patient's mouth, toward the patient's left or right ear depending on the particular preformed curvature. In another embodiment, a swivel assembly is located anywhere along the region of a bend connecting the proximal and distal ends of the tracheal tube. The swivel assembly allows the proximal end of the tracheal tube to rotate through 360° relative to the distal end. A variation of this embodiment forms the proximal end of the tracheal tube in substantially the shape of a patient's nasal cavity so that the tracheal tube may be placed in the patient's trachea through the patient's nasal cavity. In a further variation of all the embodiments, a flexible corrugated piece of tubing is attached to the proximal end of the tracheal tube.

12 Claims, 8 Drawing Sheets

*PRIOR ART*

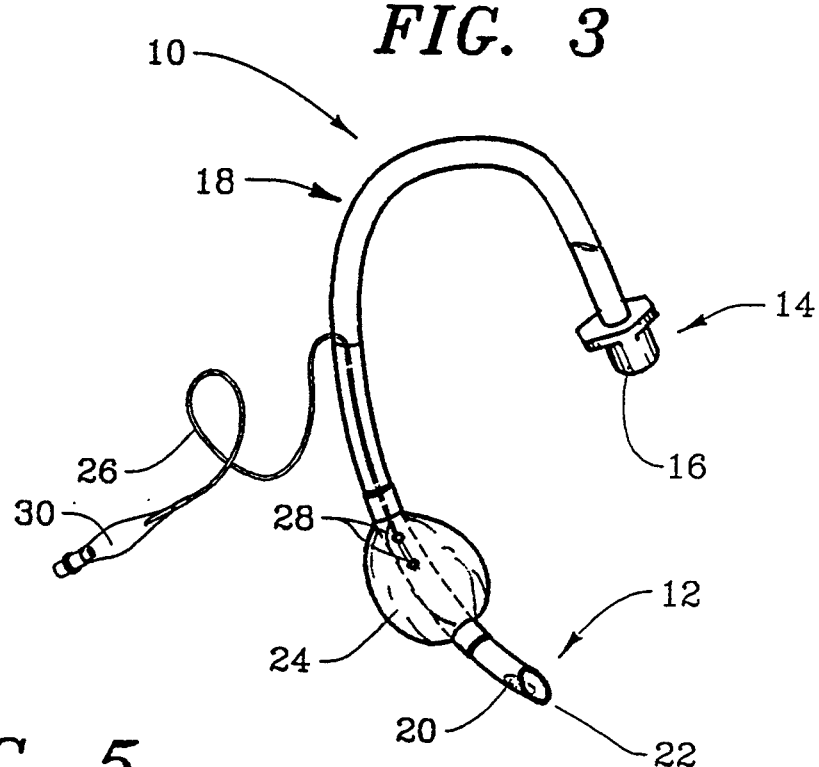
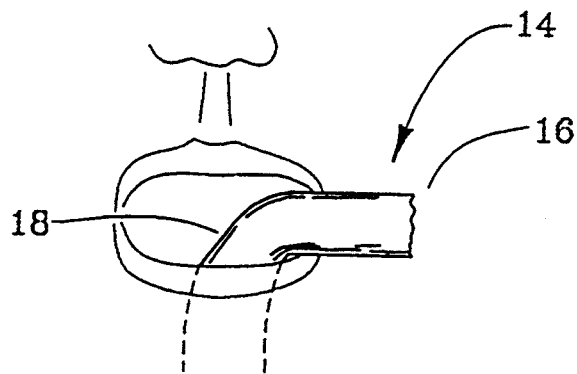
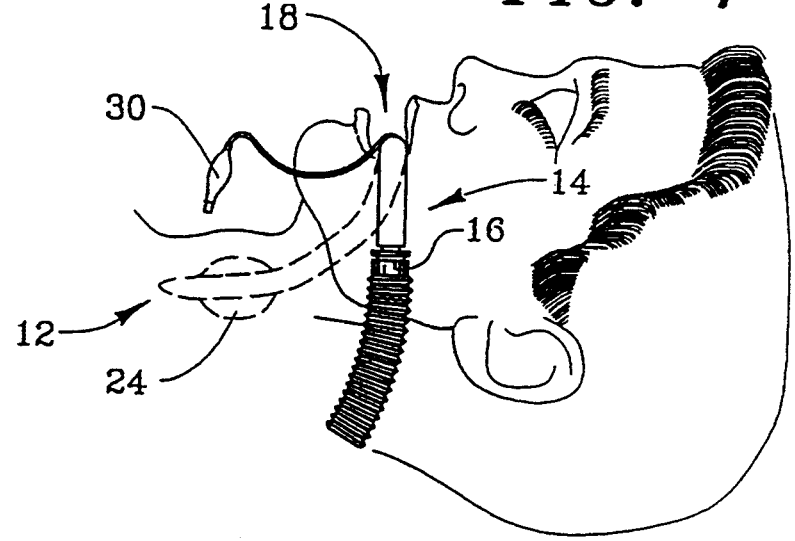

ENDOTRACHEAL TUBE FOR FACE, CHIN AND NECK SURGERY

BACKGROUND OF THE INVENTION

1. Field of the Invention

The invention relates to tracheal tubes, primarily used by anesthesiologists in the administration of anesthesia to a patient during surgery, for communicating gases and vapors through the tracheal tube to and from the trachea and more particularly to tracheal tubes that do not obscure selected areas of the patient's face, chin and neck during surgery.

2. Description of Related Art

Tracheal tubes are used in the administration of anesthesia during surgery. Typically tracheal tubes are placed through the patient's mouth and into the patient's trachea. The end of the tracheal tube that extends from the patient's mouth typically has a connector that allows the tracheal tube to be connected to a ventilator to assist the patient's breathing during the operation.

Because of the shape and alignment of the patient's mouth and trachea, tracheal tubes are constructed to conform to the configuration of the mouth and trachea. One type of tracheal tube with such a configuration, shown in FIGS. 1 and 2, is a preformed tube 1 having a large bend 2 separating a distal end 3 from a proximal end 4. The distal end 3 is formed approximately in the shape of the path between the patient's mouth and trachea. The proximal end 4 of the tracheal tube 1 contains a connector 5 that connects the tracheal tube 1 to a ventilator (not shown).

In use, as shown in FIG. 2, the distal end 3 is placed in a patient's mouth and trachea. The proximal end 4 is directed towards the patient's chest as the tube 1 exits the patient's mouth. A tracheal tube 1 having this shape is of benefit during usual facial surgery because the location of the tracheal tube 1 as it leaves the patient's mouth to connect to the ventilator does not obstruct the surgical area. However, during neck and chin surgery, the tracheal tube 1 shown in FIGS. 1 and 2 obstructs the surgical area because the tracheal tube 1 is located directly in the operating field.

SUMMARY OF THE INVENTION

In view of the foregoing, it is desirable to produce a tracheal tube having a connection to a ventilator that does not obstruct the operating field when oral or lower facial surgery is being performed.

Further, it is desirable to produce a single tracheal tube that allows the part of the tube exiting the mouth to be easily moved to various positions to facilitate free positioning or relocation of the tracheal tube during head, facial, oral or neck surgery.

In accordance with these and other desirable features and objectives, a preformed tracheal tube is provided having a distal end for placement in a patient's trachea. The tracheal tube preferably includes a beveled end and a Murphy's eye at its distal end as well as an inflatable cuff for precisely locating and positioning the distal end of the tracheal tube in the patient's trachea after insertion.

In one embodiment, the tracheal tube of the invention includes a preformed proximal end that directs the tracheal tube, upon leaving the patient's mouth, toward the patient's left or right ear depending on the particular preformed curvature. There, the ultimate proximal end may be connected to a ventilator.

In another embodiment of the tracheal tube, a swivel assembly is located anywhere along the region of the bend connecting the proximal and distal ends of the tracheal tube. The swivel assembly allows the proximal end of the tracheal tube to rotate through 360° relative to the distal end. Depending on the placement of the swivel assembly in the area around the bend, the proximal end of the tracheal tube may be rotated up to 360° around the patient's mouth without disturbing the orientation of the bevel and Murphy's eye at the distal end of the tracheal tube.

A variation of this embodiment allows the tracheal tube to be placed in a patient's trachea through the patient's nasal cavity. The distal end of the tracheal tube is the same as in the embodiment described above. The proximal end of the tracheal tube is formed to substantially conform to the shape of a patient's nasal cavity so that the tracheal tube may be placed in the patient's trachea through the patient's nasal cavity.

In a further variation of all the embodiments described above, a flexible corrugated piece of tubing is attached to the proximal end of the tracheal tube. This allows the proximal end of the tracheal tube to be connected directly to a ventilator without having to first be attached to a separate piece of flexible corrugated tubing that is connected to the ventilator.

The invention will be described in detail with particular reference to the following detailed description of the invention and with reference to the drawings where like elements are referred to by like reference numerals.

BRIEF DESCRIPTION OF THE DRAWINGS

FIG. 3 is a perspective view of one embodiment of the invention.

FIG. 4 is a side elevational view of the invention of FIG. 3 in use in a patient with the part of the tracheal tube inside the patient shown in phantom.

FIG. 5 is a top view of the invention of FIG. 3 in position in a patient during surgery with the part of the tracheal tube inside the patient shown in phantom.

DETAILED DESCRIPTION

Figure 1:
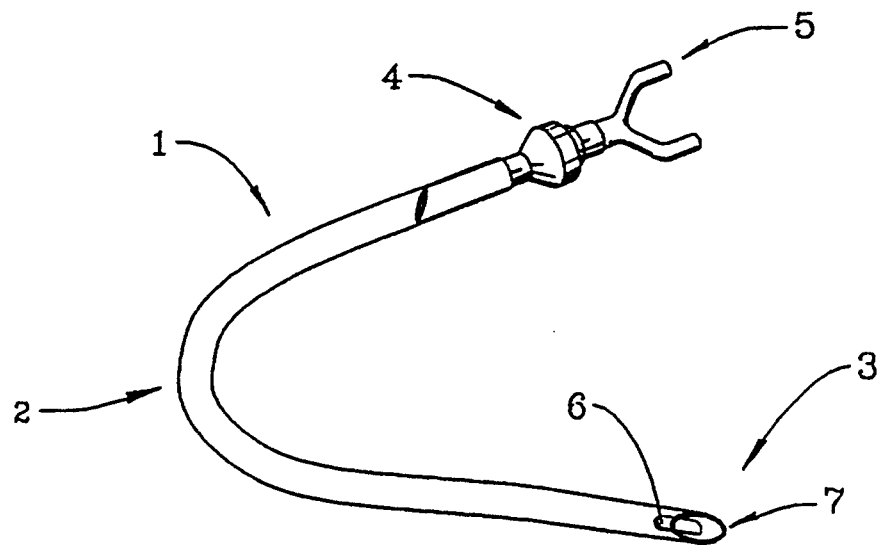
FIG. 1 is a perspective view of a prior art preformed tracheal tube.
Figure 2:
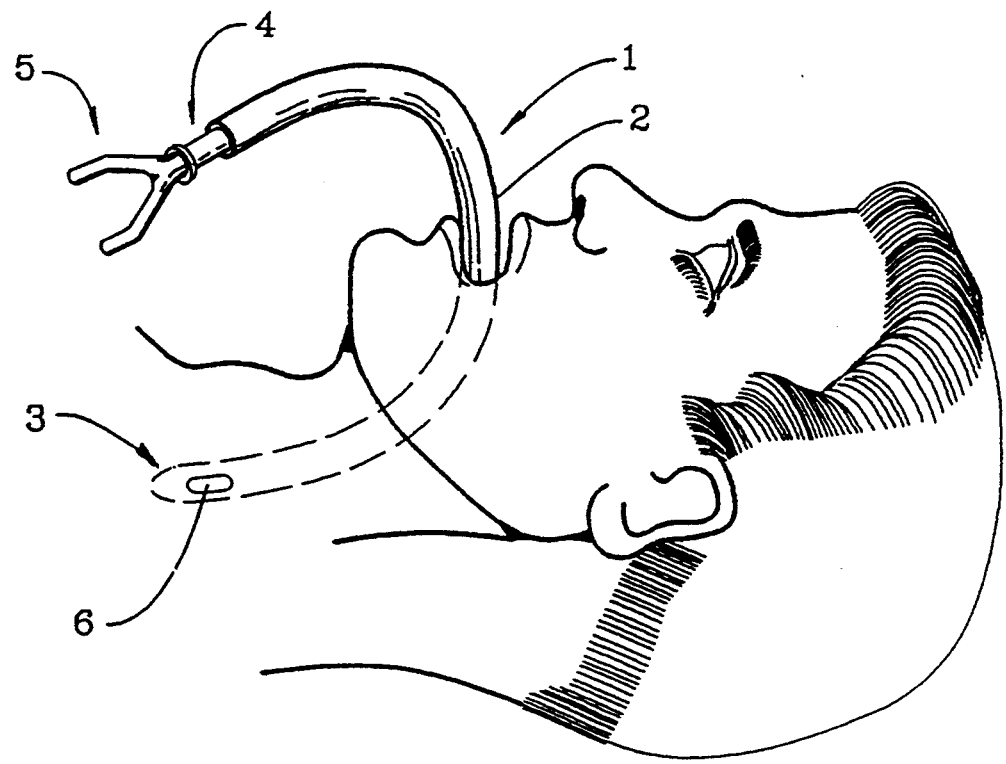
FIG. 2 is a side elevational view of the prior art tracheal tube of FIG. 1 in use in a patient with the part of the tracheal tube inside the patient shown in phantom.

One embodiment of the endotracheal tube of the invention is shown in FIG. 3 generally labeled 10. The endotracheal tube 10 includes a distal end 12 and a proximal end 14. The proximal end 14 of tube 10 ends in a connector 16 for connecting to a ventilator or similar device. In use, the proximal end 14 of tube 10 is located outside of the patient's mouth while the distal end 12 is located through the patient's mouth and trachea. A large bend 18, that will be described in more detail hereafter, connects the distal and proximal ends 12,14. The distal end 12 of the tube 10 has, at its most distal end, a Murphy's eye 20 and a bevel end 22.

An inflatable cuff 24 is located proximal to the Murphy's eye 20. The cuff 24, when inflated, securely locates the distal end 12 in a patient's trachea, as is well understood in the art. An inflation tube 26 for inflating cuff 24 is provided. Inflation tube 26 has inflation openings 28 within cuff 24 and a closeable valve 30 at its end opposite cuff 24. Inflation tube 26 allows air under pressure to be passed through valve 30 into inflation tube 26 and expelled through inflation openings 28 to inflate cuff 24.

As better shown in FIGS. 4 and 5, the bend 18 is curved so that when the distal end 12 of tube 10 is placed in the patient's trachea, the tube 10 upon exiting the patient's mouth is directed at substantially a right angle to the plane containing the distal end 12. In addition, the tube 10, after exiting the patient's mouth at substantially a right angle to the plane of distal end 12, is curved downward, that is in a direction toward the patient's back. This causes the proximal end 14 of the tube 10 to traverse the patient's cheek (in FIG. 4, the patient's left cheek) upon exiting the patient's mouth. Although the proximal end 14 is shown in FIG. 4 traversing the patient's left cheek, by reversing the curve on bend 18, the tube 10 may be made so that proximal end 14 traverses the patient's right cheek. This configuration allows the tube 10 to be connected to a ventilator or similar device through connector 16 while leaving the patient's chin and neck area unobstructed by the proximal end 14 of the tube 10.

Figure 6:
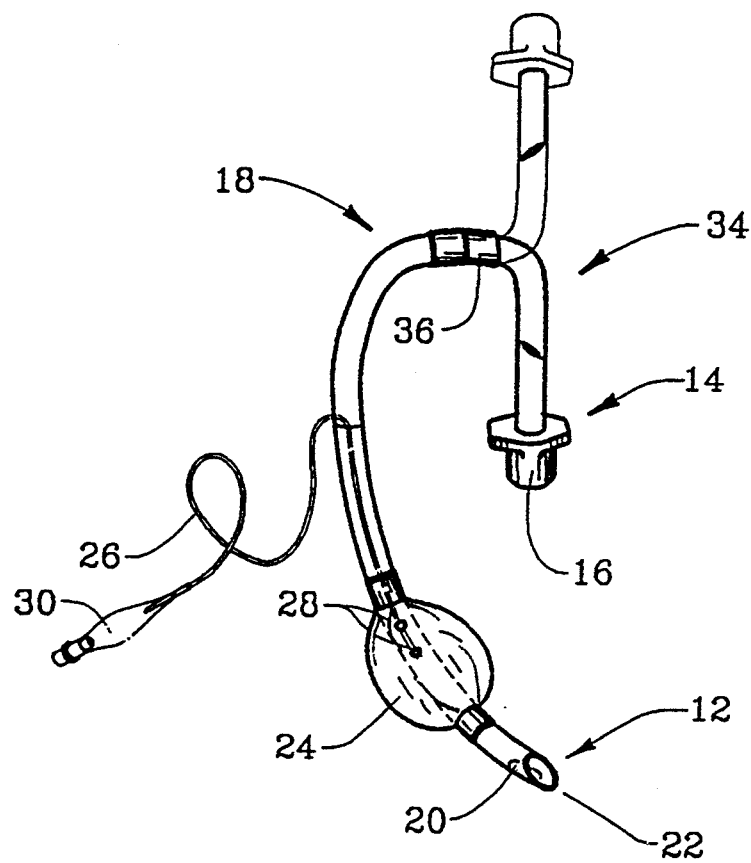
FIG. 6 is a perspective view of another embodiment of the invention with a various possible position of the tracheal tube shown in phantom.
Figure 7:
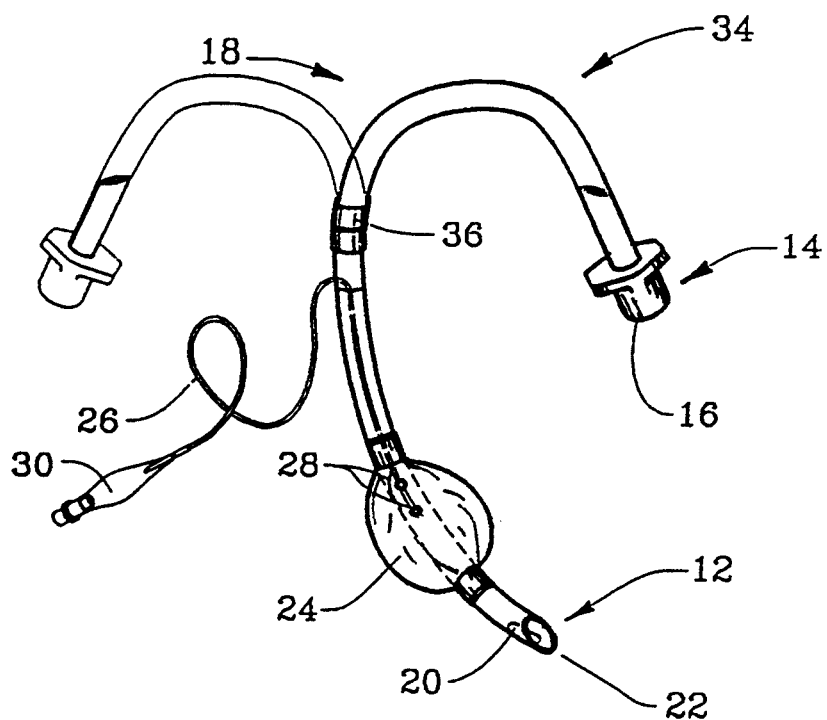
FIG. 7 is a perspective view of another embodiment of the invention with a various possible position of the tracheal tube shown in phantom.

FIGS. 6 and 7 show two variants of an alternate embodiment of the invention. In FIGS. 6 and 7, similar elements are referred to by similar numbers. The elements shown in FIGS. 6 and 7 that are similar to those described in connection with the embodiment described above are labeled with similar numbers.

In both FIGS. 6 and 7, the endotracheal tubes are generally labeled 34. As can be seen, the endotracheal tubes 34 have a distal end 12 and a proximal end 14 with a bend 18 connecting the distal end 12 to the proximal end 14. Both endotracheal tubes 34 have a Murphy's eye 20 and a bevel 22 located at the most distal end of distal end 12. Further, an inflation cuff 24 having an inflation tube 26, inflation openings 28, and a valve 30 as described above is combined with the endotracheal tubes 34.

Figure 13:
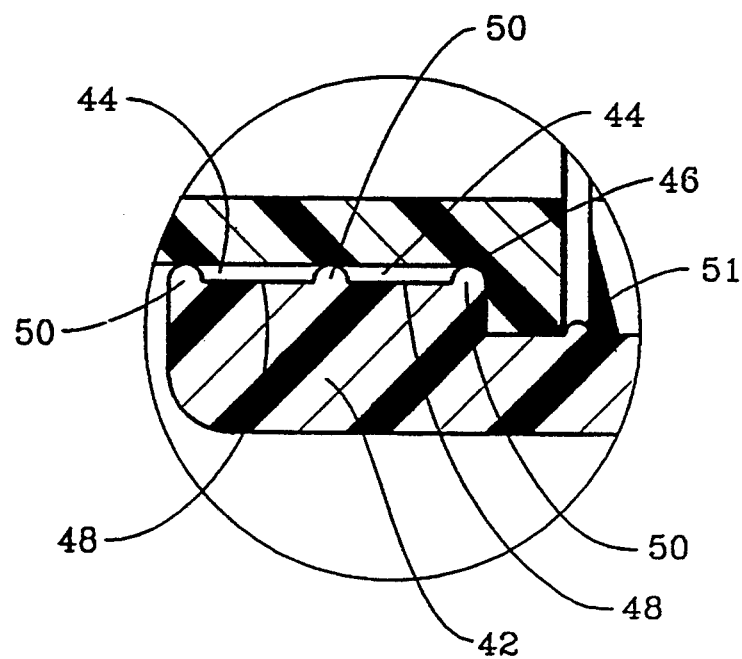
FIG. 13 is a close up view of the area labeled 13 in FIG. 12.
Figure 14:
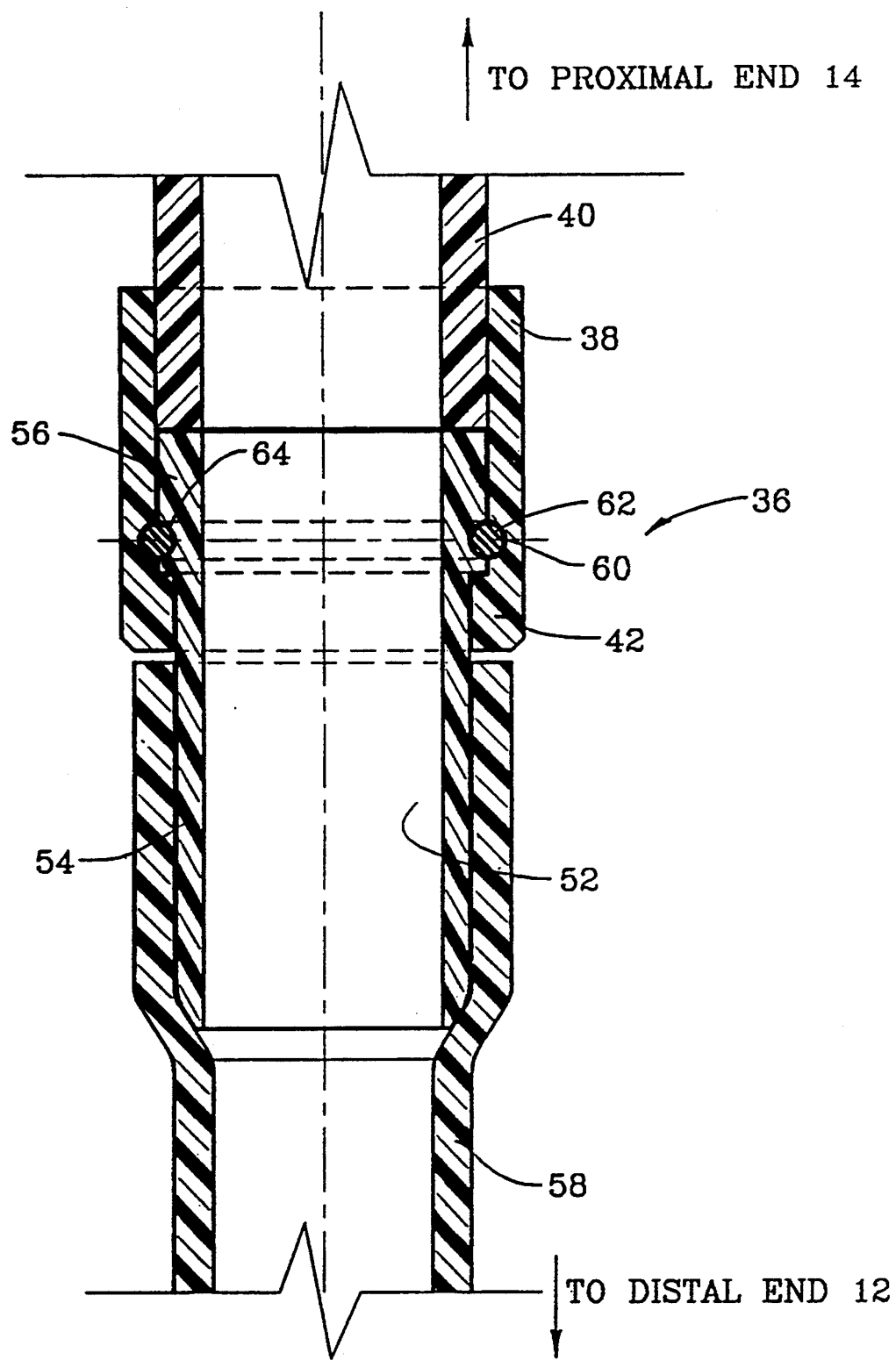
FIG. 14 is a cross-sectional view of one embodiment of the swivel used in the embodiments of FIGS. 6 and 7.

In these embodiments, a swivel 36 is located along the endotracheal tube 34 near the bend 18. The swivel provides a virtually gas-tight seal across its length and allows the proximal end 14 of endotracheal tube 34 to rotate 360° relative to the distal end 12. The details of the preferred embodiment of the swivel 36 is shown in detail in FIGS. 12, 13. An alternate embodiment is shown in FIG. 14. In these Figures, like elements are referred to by like reference numbers.

Figure 12:
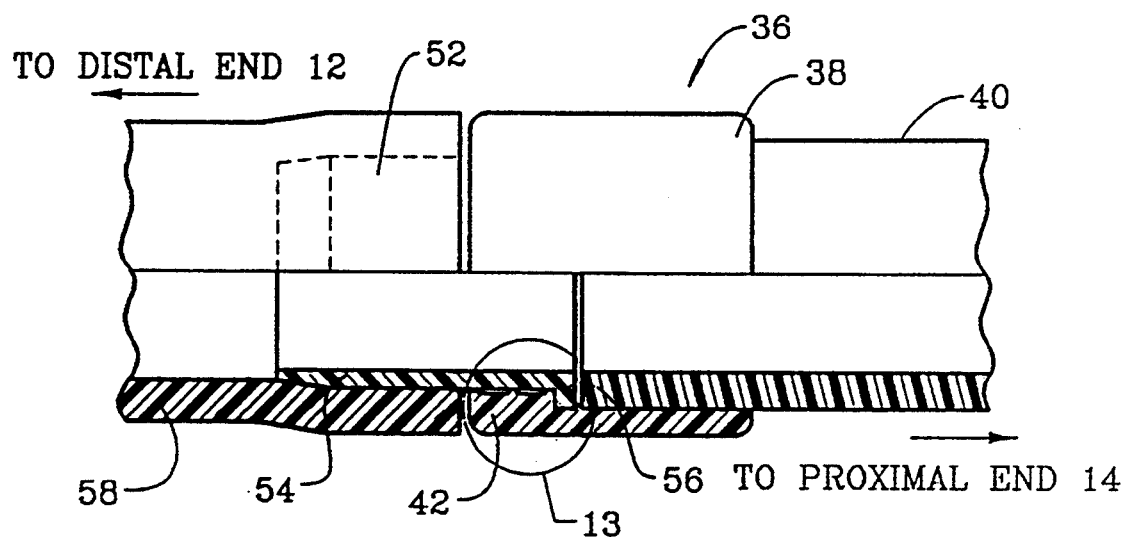
FIG. 12 is a cross-sectional view of the preferred embodiment of the swivel used in the embodiments of FIGS. 6 and 7.

In FIGS. 12 and 14, the swivel is generally labeled 36. A cylindrical outer case 38, made of a rigid material, is attached to the outer surface of the proximal side piece 40 of the endotracheal tube 34 by means well known in the art. Outer case 38 includes an inwardly extending annular ledge 42 that extends from the distal end of outer case 38.

In the preferred embodiment of FIG. 12, outer case 38 includes a pair of indents 44 extending into outer case 38 entirely around the inside surface 46 of ledge 42. Indents 44 have a substantially planar elongated surface 48 opposite inside surface 46 of outer case 38. Protrusions 50 are formed between and on the ends of indents 44. Protrusions 50 extend from the planar elongated surface 48 to the inside surface 46. An inwardly extending annular ring 51 extends into the central area of outer case 38 a small distance proximal to ledge 42 for a purpose that will be explained hereafter.

A cylindrical inner core 52, also made of a rigid material, is provided having an elongated body 54 and an outwardly extending expanded flat annular lip 56 at the proximal end of elongated body 54. Lip 56 has an outer diameter approximately equal to the inner diameter of outer case 38 proximal to lip 56. The diameter of body 54 is approximately equal to the diameter of inner core 52 across ledge 42.

Distal side piece 58 of endotracheal tube 34 is placed over and attached to the distal end of elongated body 54 by means well known in the art. The connection between distal side piece 58 and body 54 provides a virtually gas-tight seal so that any gas present within the central lumen of distal side piece 58 cannot escape through the connection between distal side piece 58 and body 54.

Indents 44 are filled with a lubricous material such as petroleum jelly or similar gel-like gasket forming material. Inner core 52 is concentrically placed within outer case 38 so that the distal side of lip 56 contacts the proximal end of ledge 42. Lip 46 is located distal to but abutted with annular ring 51.

The combination of indents 44, protrusions 50 and the petroleum jelly or other similar material forms a gel gasket between outer case 38 and inner core 52. The petroleum jelly in indents 44 prevents gases present within the main lumen of endotracheal tube 34 from escaping through the interface between the inner core 52 and outer case 38 and also lubricates the rotation of inner core 52 inside outer case 38.

Inner core 52 may be rotated around its central axis relative to outer case 38, or vice versa. Contact between annular ring 51 and the proximal end of lip 56 prevents inner core 52 from moving proximally relative to outer case 38 while the contact of lip 56 and ledge 42 keeps inner core 52 from moving distally relative to outer case 38. As stated above, the petroleum jelly in indents 44 prevents gases present within the main lumen of endotracheal tube 34 from escaping through the interface between the inner core 52 and outer case 38.

In the embodiment shown in FIG. 14, in place of the indents 44 of the embodiment of FIG. 12, outer case 38 includes a single indent 60 extending into outer case 38 entirely around the inside surface of outer case 38 just proximal to ledge 42. Indent 60 is for encasing an O-ring 62 as will be described hereafter.

Cylindrical inner core 52, as described above, has distal side piece 58 of endotracheal tube 34 placed over and attached to the distal end of elongated body 54 by means well known in the art. The connection between distal side piece 58 and body 54 provides a virtually gas-tight seal so that any gas present within the central lumen of distal side piece 58 cannot escape through the connection between distal side piece 58 and body 54.

Inner core 52 includes an indent 64 extending into and entirely around lip 56. An 0-ring 62 is placed around indent 64. Then inner core 52 is concentrically placed within outer case 38 so that lip 56 contacts ledge 42. Indent 64 is located in inner core 52 so that indent 64 is aligned with indent 60 so that 0-ring 62 provides a virtually gas-tight seal between the interior and exterior of outer case 38 and inner core 52. 0-ring 62 prevents gases present within the main lumen of endotracheal tube 34 from escaping through the interface between the inner core 52 and outer case 38.

Inner core 52 may be rotated around its central axis relative to outer case 38, or vice versa. O-ring 62 prevents inner core 52 from moving proximally relative to outer case 38 while the contact of lip 56 and ledge 42 keeps inner core 52 from moving distally relative to outer case 38. As stated above, O-ring 62 also prevents gases present within the main lumen of endotracheal tube 34 from escaping through the interface between the inner core 52 and outer case 38.

In both embodiments of swivel 36, because swivel 36, along with the distal end 12 of endotracheal tube 34, must be placed either in or near the patient's mouth, the outside diameter of swivel 36 should be minimized in order to avoid damage to the mouth or teeth or difficulty in placing or removing the tracheal tube 34. Preferable, the outside diameter of swivel 36 should be approximately the same as the outside diameter of tracheal tube 34. In addition, the inside diameter of inner core 52 should be approximately the same diameter as the diameter of the lumen of endotracheal tube 34 so that swivel 36 does not restrict the flow of gases through the endotracheal tube 34.

Figure 8:
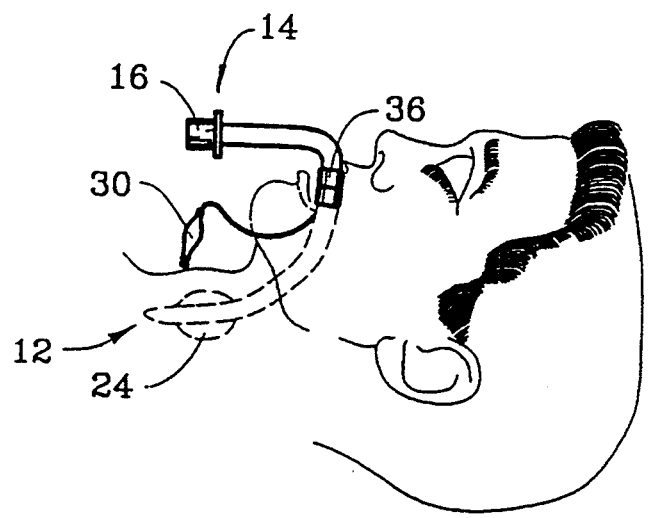
FIG. 8 is a side elevational view of the invention of FIG. 6 in use in a patient with the part of the tracheal tube inside the patient shown in phantom.
Figure 10:
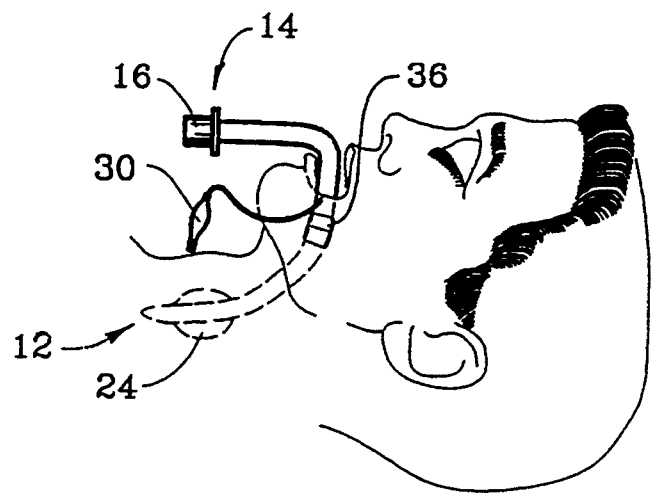
FIG. 10 is a side elevational view of the invention of FIG. 7 in use in a patient with the part of the tracheal tube inside the patient shown in phantom.

As seen in FIGS. 6 and 7, the location of swivel 36 in FIG. 6 is located distal to bend 18 while the location of swivel 36 in the embodiment of FIG. 7 is located approximately at the bend 18. The location of the swivel 36 and the orientation of tube 34 in or near the patient's trachea or mouth in the vicinity of their respective swivels 36 (FIGS. 8 and 10) may limit rotation of the proximal end 14 as it leaves the patient's mouth.

Figure 9:
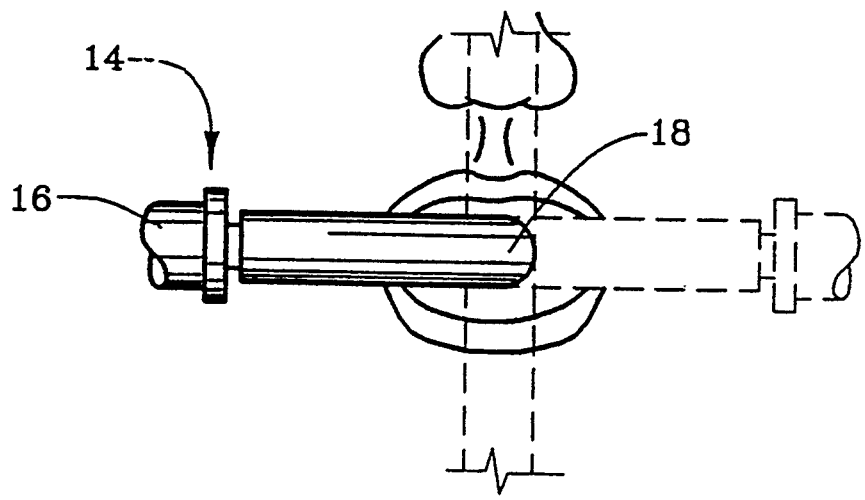
FIG. 9 is a top view of the invention of FIG. 6 in position in a patient during surgery with various possible positions of the tracheal tube shown in phantom.

As shown in FIG. 9, in the embodiment of FIG. 6, because the swivel 36 is placed further along the bend 18 near the patient's teeth and approximately perpendicular to a plane containing the patient's mouth, the proximal end 14 of tube 34 may be rotated approximately 360° around swivel 36.

Figure 16:
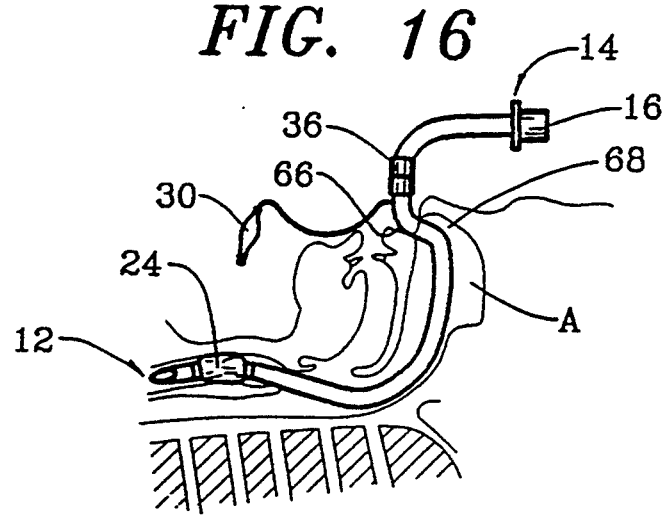
FIG. 16 is a cross-sectional view of the invention of FIG. 15 in use in a patient's nasal cavity.
Figure 11:
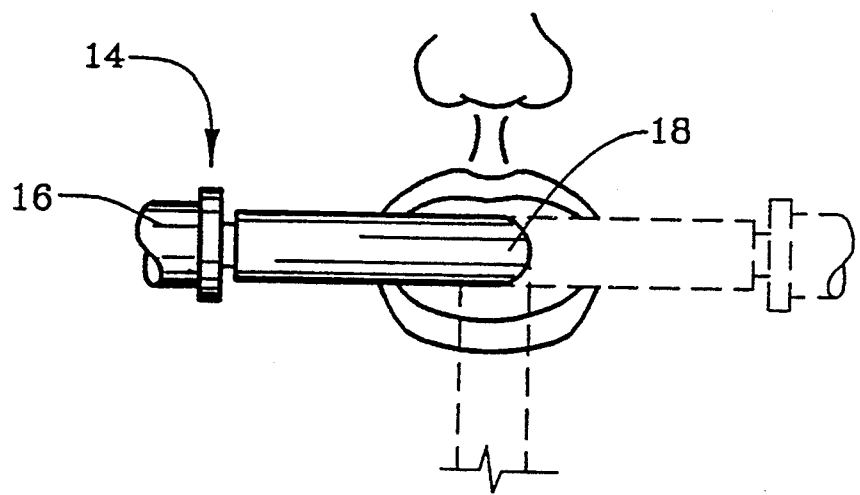
FIG. 11 is a top view of the invention of FIG. 7 in position in a patient during surgery with various possible positions of the tracheal tube shown in phantom.
Figure 15:
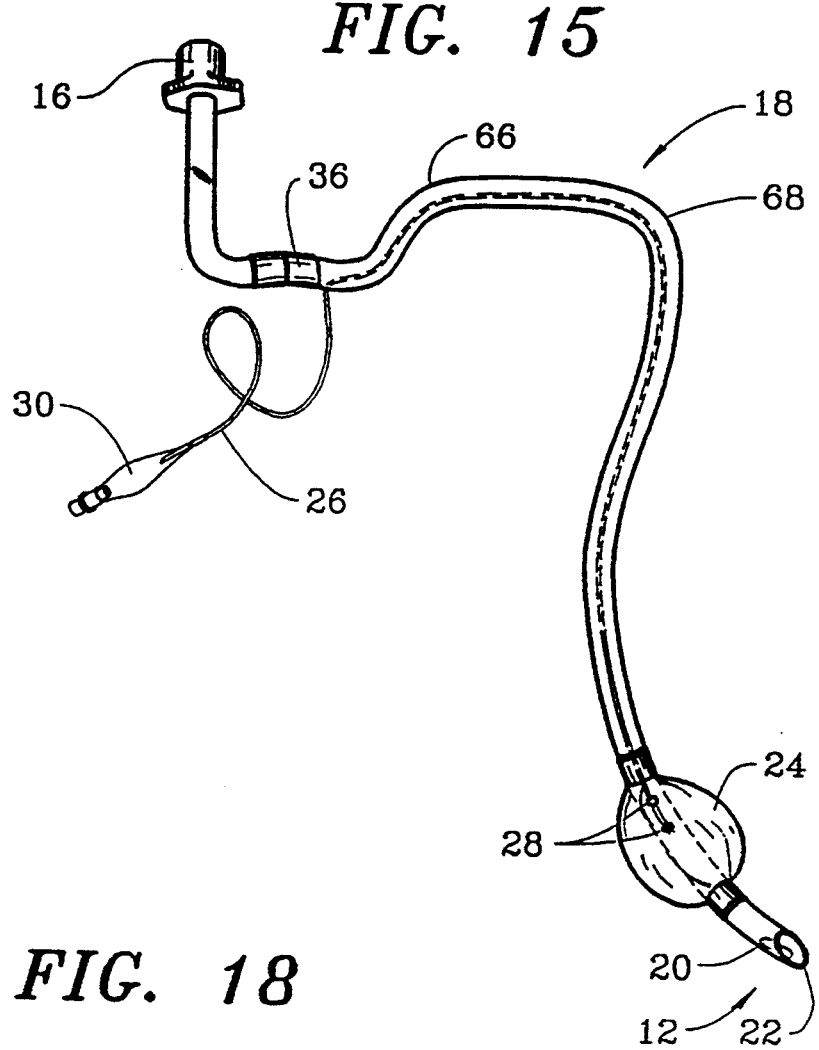
FIG. 15 is a perspective view of another embodiment of the invention.

In FIG. 11, the limits of rotation of the proximal end 14 of the embodiment shown in FIG. 7 is shown. As can be seen, because swivel 36 is located in the patient's oral cavity, the proximal end 14 of tube 34 may swivel only approximately 180° from the left side of a patient's mouth across the patient's chin to the right side of the patient's mouth. In both embodiments shown in FIGS. 6 and 7, the proximal end 14 of tube 34 may be moved to any position within the limits of rotation of the proximal end 14 that the surgeon desires, FIG. 15 shows a perspective view of a variation of the embodiments of FIGS. 6 and 7 for placement in a patient's nasal cavity. Insofar as the embodiment shown in FIG. 15 is similar to the embodiment shown in FIGS. 6 and 7, similar elements have been referred to by similar reference numbers. The device of FIG. 15 is a tracheal tube intended to be placed in the patient's trachea through a patient's nasal cavity as shown in FIG. 16. As can be seen, in this embodiment the distal end 12 of the endotracheal tube 34 extends through the patient's nasal cavity A into the patient's trachea.

To conform to the shape of a patient's nasal cavity, the large bend 18 connecting the distal end 12 to the proximal end 14 is modified from the shape of the embodiments of FIGS. 6 and 7. In order for the distal end 12 of the tracheal tube 34 to be more easily placed through the patient's nasal cavity, the distal end 12 has a first bend 66 distal to the swivel 36 in a direction toward the top of the patient's head. Endotracheal tube 34 has a second bend 68 distal to the first bend 66 that gradually curves the distal part of endotracheal tube 34 distal to second curve 68 in a shape substantially conforming with a normal patient's nasal cavity so that the ultimate distal end 12 of endotracheal tube 34 is placed in a patient's trachea. In all other ways, the nasal embodiment is similar to the embodiment shown in FIGS. 6 and 7.

Figure 17:
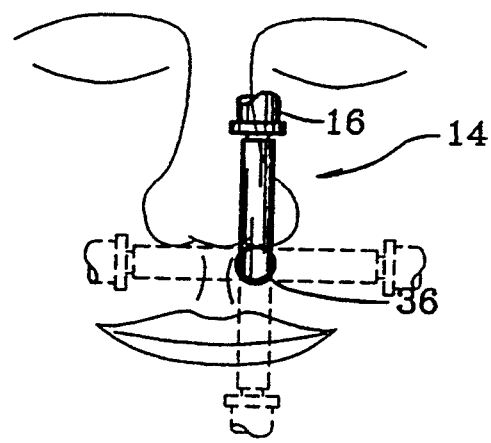
FIG. 17 is a top view of the invention of FIG. 15 in position in a patient during surgery with various possible positions of the tracheal tube shown in phantom.

FIG. 17 shows the nasal endotracheal tube 34 in position extending out of a patient's nose. As can be seen, the swivel 36 is located proximally to the patient's nose so that the proximal end 14 of endotracheal tube 34 may be rotated around 360°. In this way, the proximal end 14 may be positioned in any number of desired positions.

Figure 18:
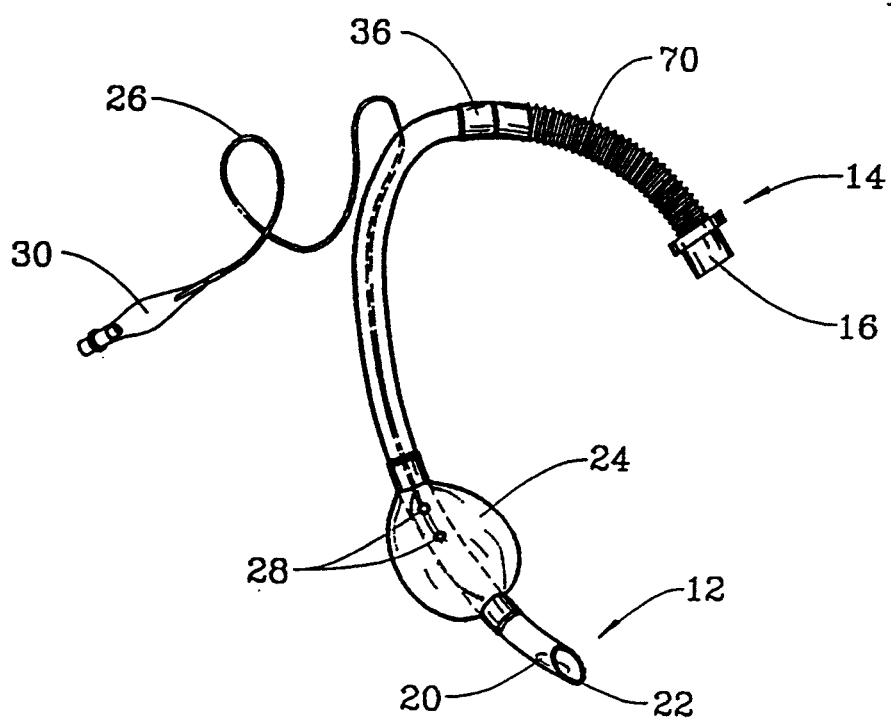
FIG. 18 is a perspective view of another alternate embodiment of the invention.

FIG. 18 shows another embodiment of the invention shown in FIGS. 6, 7 and 15. A flexible corrugated tube 70 is attached proximal to swivel 36 and distal to connector 16. The corrugated tube 70 allows the proximal end 14 of endotracheal tube 34 to be variable in length as is helpful in attachment to a ventilator. In this way, the corrugated section usually connected between connector 16 and the ventilator is not required as the desired flexibility is attained through the corrugated tube 70.

Tubes 10, 34 and 70 are preferably made of a flexible polymer material such as polyvinylchloride (PVC), polyethylene or silicone. In addition, tubes 10, 34 and 70 may be reinforced by means well understood in the art. Outer case 38 and inner core 52 are both preferably made of polyvinylchloride (PVC) although and other rigid material suitable for use in medical devices may be used. For example, outer case 38 and inner core 52 may both be made of a metal such as stainless steel or a ceramic material. These materials being merely illustrative of materials, among others, that will occur to those skilled in the art. Tubes 10, 34 and 70 may be made according to techniques common for making standard prior art endotracheal tubes.

Although specific embodiments of swivel 36 have been described herein, other embodiments of swivel 36 may be used as desired. The key features of the swivel 36 being that the proximal end 14 may be rotated relative to the distal end 12; a gas tight seal is formed between the interior and exterior of the endotracheal tube 34 at swivel 36; and, the outside and inside diameters of swivel 36 are approximately the same as the outside and inside diameters of endotracheal tube 34.

The invention has been described above in connection with specific embodiments. However, the description contained herein is given for the purpose of illustration and not for the purpose of limitation. Changes and modifications may be made to the description contained herein and still be within the scope of the invention. Further, obvious changes and modifications will occur to those skilled in the art.

What is claimed is:

1. An endotracheal tube comprising:
    a) an elongated tube having a distal and a proximal end and a central lumen extending from said distal to said proximal end of said tube, said distal end formed having substantially the curvature of a human trachea, said distal end placeable in a patient's trachea, said tube also having at least one bend between said distal end and said proximal end, said bend formed to position said proximal end to exit the patient through the patient's mouth when said distal end is positioned in the patient's trachea;
    b) means for fluidly communicating said central lumen with the exterior of said tube at said distal end of said tube; and,
    c) means for positioning said proximal end of said tube to selectively expose a patient's neck, chin or face during surgery, said means for positioning comprising a swivel for rotating said proximal end relative to said distal end, said swivel located along said tube between said distal and said proximal ends, said swivel located along said tube distal to or approximately at said bend in said tube.

2. The endotracheal tube of claim 1 wherein said swivel is located along said tube so that when said distal end is positioned in the patient's trachea, said tube extends through the patient's mouth and said swivel is located in the patient's mouth.

3. The endotracheal tube of claim 1 wherein said swivel is located along said tube so that when said distal end is positioned in the patient's trachea, said tube extends through a patient's mouth and said swivel is located outside of the patient's mouth.

4. The endotracheal tube of claim 1 wherein said proximal end of said tube includes a flexible corrugated section to allow said proximal end to be more easily moved into a desired position.

5. The endotracheal tube of claim 1 further comprising means for retaining said distal end of said tube within a patient's trachea.

6. The endotracheal tube of claim 1 wherein said swivel includes:
    a) a substantially cylindrical case having an inwardly extending annular ledge at a first end and connected to said proximal end of said tube at an opposed second end, said case having a first inner diameter and said ledge having a second inner diameter smaller than said first inner diameter, said case having a lumen extending from said first to said second end of said case;
    b) a substantially cylindrical core having an outwardly extending annular lip at a first end and connected to said distal end of said tube at an opposed second end, said core having a first outer diameter approximately equal to said second inner diameter, said lip having a second outer diameter larger than said first outer diameter and approximately equal to said first inner diameter, said core placed concentrically within said case so that said lip contacts said ledge and said core extends through said ledge, said core having a lumen extending from said first end to said second end of said core, whereby said core rotates around its axis within said case and a continuous lumen is formed through said case and said core;
    c) means for providing a virtually gas-tight seal between said core and said case.

7. The endotracheal tube of claim 6 wherein said means for providing a virtually gas-tight seal comprises:
    a) at least one annular groove extending into said ledge from said lumen extending through said case, said groove opposite said core; and
    b) a gel-like gasket forming material placed within said groove, said gel-like gasket forming material contacting said core.

8. The endotracheal tube of claim 7 wherein said gel-like gasket forming material is petroleum jelly.

9. The endotracheal tube of claim 6 wherein said means for providing a virtually gas-tight seal comprises:
    a) an O-ring surrounding said core; and,
    b) means for positioning said O-ring adjacent said ledge and in contact with said core.

10. The endotracheal tube of claim 9 wherein said means for positioning said O-ring comprises a groove extending into said core and an opposed groove extending into said ledge and wherein said O-ring is placed in said groove.

11. An endotracheal tube comprising:
    a) an elongated tube having a distal and a proximal end and a central lumen extending from said distal to said proximal end of said tube, said distal end formed having substantially the curvature of a human trachea, said distal end placeable in a patient's trachea, said tube also having at least one bend between said distal end and said proximal end, said bend formed to position said proximal end to exit the patient through the patient's mouth when said distal end is positioned in the patient's trachea, said proximal end of said tube including a flexible corrugated section to allow said proximal end to be more easily moved into a desired position;
    b) means for fluidly communicating said central lumen with the exterior of said tube at said distal end of said tube; and,
    c) means for positioning said proximal end of said tube to selectively expose a patient's neck, chin or face during surgery, said means for positioning comprising a means for rotating said proximal end relative to said distal end, said means for rotating located along said tube between said distal and said proximal ends.

12. An endotracheal tube comprising:
    a) an elongated tube having a distal and a proximal end and a central lumen extending from said distal to said proximal end of said tube, said distal end formed having substantially the curvature of a human trachea, said distal end placeable in a patient's trachea, said tube also having at least one bend between said distal end and said proximal end, said bend formed to position said proximal end to exit the patient through the patient's mouth when said distal end is positioned in the patient's trachea, said proximal end of said tube including a flexible corrugated section to allow said proximal end to be more easily moved into a desired position;

b) means for fluidly communicating said central lumen with the exterior of said tube at said distal end of said tube; and, c) means for positioning said proximal end of said tube to selectively expose a patient's neck, chin or face during surgery, said means for positioning comprising a swivel for rotating said proximal end relative to said distal end, said swivel located along said tube between said distal and said proximal ends, said swivel including:

i) a substantially cylindrical case having an inwardly extending annular ledge at a first end and connected to said proximal end of said tube at an opposed second end, said case having a first inner diameter and said ledge having a second inner diameter smaller than said first inner diameter, said case having a lumen extending from said first to said second end of said case;

ii) a substantially cylindrical core having an outwardly extending annular lip at a first end and connected to said distal end of said tube at an opposed second end, said core having a first outer diameter approximately equal to said second inner diameter, said lip having a second outer diameter larger than said first outer diameter and approximately equal to said first inner diameter, said core placed concentrically within said case so that said lip contacts said ledge and said core extends through said ledge, said core having a lumen extending from said first end to said second end of said core, whereby said core rotates around its axis within said case and a continuous lumen is formed through said case and said core; and, iii) means for providing a virtually gas-tight seal between said core and said case comprising:

A) at least one annular groove extending into said ledge from said lumen extending through said case, said groove opposite said core; and, B) a gel-like gasket forming material placed within said groove, said gel-like gasket forming material contacting said core; and, d) means for retaining said distal end of said tube within a patient's trachea.

* * * * *